US00PP19537P2

(12) United States Plant Patent
Bradford

(10) Patent No.: US PP19,537 P2
(45) Date of Patent: Dec. 2, 2008

(54) INTERSPECIFIC TREE NAMED 'BLACKRED I'

(50) Latin Name: *Prunus*
Varietal Denomination: Blackred I

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 11/984,892

(22) Filed: Nov. 26, 2007

(51) Int. Cl.
*A01H 5/00* (2006.01)

(52) U.S. Cl. ..... Plt./180
(58) Field of Classification Search ..... Plt./180
See application file for complete search history.

(56) References Cited

U.S. PATENT DOCUMENTS

PP7,503 P 4/1991 Bradford
PP15,809 P2 6/2005 Bradford

*Primary Examiner*—Annette H Para
*Assistant Examiner*—S. B. McCormick-Ewoldt

(57) ABSTRACT

The present invention relates to an interspecific tree and more particularly to a new and distinct variety broadly characterized by a medium size, vigorous, hardy, and productive tree. The variety is self-unfruitful, blooms during the early season, and produces an abundance of blossoms and pollen. The fruit matures under the ecological conditions described during early June, with first picking on Jun. 1, 2007. The fruit is uniformly medium, in size, nearly black in skin color, clingstone in type, oblate in shape, full red in flesh color, firm and crisp in texture, and good in flavor.

1 Drawing Sheet

Botanical classification: *Prunus* sp.
Varietal denomination: 'Blackred I'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits. The present invention relates to a new and distinct variety of interspecific tree, which has been denominated varietally as 'Blackred I'.

During a typical blooming season I isolate as seed parents both individual and groups of different plum trees by covering them with screen houses. A hive of bees is placed inside each such house, and bouquets to provide pollen from different plum, apricot, and interspecific plum-apricot hybrid trees are placed in buckets near the trees approximately every two days for the duration of the bloom. During 2001 one tree of 'Purple Majesty' (U.S. Plant Pat. No. 7,503) plum was crossed by me in this manner. To pollinate this isolated tree, I selected bouquets from several sources of apricot and interspecific plum-apricot hybrid trees without keeping specific written details. Upon reaching maturity the fruit from this plum tree was harvested and the seeds were removed, cracked, stratified and germinated as a group with the label "H1". They were grown as seedlings on their own root in my greenhouse and upon reaching dormancy transplanted to a cultivated area of my experimental orchard located near Le Grand, Calif. in Merced County (San Joaquin Valley). During the spring of 2004 the claimed variety was selected by me a single plant from the group of seedlings described above. Subsequent to origination of the present variety of interspecific tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'Purple Majesty' (U.S. Plant Pat. No. 7,503) plum, by being self-unfruitful and by producing fruit that is similar in size, clingstone in type, oblate in shape, and good in flavor, but is quite distinguished therefrom by producing fruit that is nearly black in skin color, that has less skin freckling, that is full red in skin color instead of orange yellow, and that matures about thirty-five days earlier.

The present variety is more similar to 'YUMMY® gem' (U.S. Plant Pat. No. 15,809) plum by being self-unfruitful, by blooming during the early season, and by producing fruit that is almost black in skin color, but is distinguished therefrom by producing fruit that is larger in size, oblate instead of globose in shape, and fully red in flesh color instead of yellow.

SUMMARY OF VARIETY

The present interspecific variety is characterized by a medium size, vigorous, hardy, and productive tree. Being self-unfruitful, the present variety requires cross pollination from an apricot, interspecific, or plum that blooms during the early season. The present variety's abundance of blossoms and pollen entices strong bee activity to facilitate pollination. The fruit matures under the ecological conditions described during the early June, with first picking on Jun. 1, 2007. The fruit is uniformly medium in size, nearly black in skin color, clingstone in type, oblate in shape, full red in flesh color, firm and crisp in texture, and good in flavor.

DRAWING

The accompanying photograph consists of four whole fruits positioned to display the characteristics of the skin color and form, one half of a fruit divided transversely to the suture plane to reveal the flesh and stone, a freshly cleaned stone, a young tip shoot growth, typical leaves, and two insets depicting the flower buds and blossoms as they appeared on the tree during the blooming season.

DETAILED BOTANICAL DESCRIPTION

Referring now more specifically to the pomological characteristics of this new and distinct variety of interspecific tree, the following has been observed under the ecological conditions prevailing near Le Grand, Merced County (San Joaquin Valley), Calif. The fruit description was developed at the state of full ripe on Jun. 12, 2007, on the original tree during its sixth growing season. The flower and bud descriptions were developed during the previous blooming season. All major color code designations are by reference to the Inter-Society Color Council, National Bureau of Standards. Common color names are also used occasionally.

Parentage

Seed parent: 'Purple Majesty' plum (U.S. Plant Pat. No. 7,503).

Pollen parent: Unknown.

Tree

Size: Medium, reaching and maintaining a height of 12' [3.66 m.] and a spread of 7' [2.13 m.] after six growing seasons utilizing typical dormant pruning.

Vigor: Vigorous, responding typically to irrigation and fertilization. The variety grows about 4° [1.22 m.] of surplus top-growth during the spring and summer. The plant should be grown on a standard commercial rootstock for production purposes.

Growth: Upright and dense.

Form: Central leader type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning usually necessary.

Fertility: Self-unfruitful, requiring cross pollination by a suitable early seasonal blooming apricot, interspecific, or plum, such as 'Yummy® gem' (U.S. Plant Pat. No. 15,809).

Bearing: Regular bearer, with no crop failures observed.

Trunk:

- *Size.*—Large, reaching a maximum diameter of 5" [127 mm.] after the sixth growing season.
- *Texture.*—Shaggy.
- *Bark color.*—A Dark grayish brown [62. d.gy.Br] and Grayish brown [61. gy.Br.] variegation with Dark orange yellow [72. d.OY] crevices present.
- *Lenticels.*—Approximate Number Per Square Inch: 5. Color: Dark orange yellow [72. d.OY]. Average Size: ⅜" [9.5 mm.]. Shape: Eye-shaped, elongated.

Branches:

- *Size.*—Diameter of lowest limb is 1¾" [44.5 mm.] measured 12" from central leader.
- *Texture.*—Smooth on first and second year wood, increasing roughness with age.
- *Color.*—1st Year Wood Topside: Moderate olive [107. m.Ol]. 1st Year Wood Underside: Strong yellow green [117. s.YG]. Older Wood: Strong yellowish brown [74. s.yBr].
- *Lenticels.*—Number Per Square Inch: More than 60 on second year wood. Color: Pale orange yellow [73. p.OY]. Average size: 1/64" [0.4 mm.]. Shape: Elongated, rectangular.

Leaves:

- *Size.*—Medium. Average Length: 3 ⅞" [98 mm.]. Average width: 1⅝" [41 mm.].
- *Arrangement.*—Alternate.
- *Thickness.*—Medium.
- *Form.*—Elliptical.
- *Apex.*—Acuminate.
- *Base.*—Acute with an average angle base angle of 65 to 70 degrees.
- *Surface.*—Smooth.
- *Color.*—Dorsal Surface: Moderate olive green [125. m.OlG]. Ventral Surface: Moderate yellow green [120. m.YG].
- *Margin.*—Finely serrate.
- *Venation.*—Pinnately net veined.
- *Petiole.*—Average Length: ⅜" [9.5 mm.]. Average Thickness: 1/16" [1.6 mm.]. Color: Light yellow green [119. l.YG] with some Light reddish brown [42. l.rBr] where exposed to the sun.
- *Stipules.*—Number: 2 per leaf, up to 6 per growing tip. Average Length: ¼" [6.4 mm.]. Color: Brilliant yellow green [116. brill.YG] becoming Dark reddish brown [44. d.rBr] with age.
- *Glands.*—Number: Mostly 2 per leaf. Position: Alternately positioned at the intersection of the petiole and the leaf blade. Size: Medium. Form: Globose. Color: Light yellow green [119. l.YG] becoming Moderate reddish brown [43. m.rBr] with age.
- *Leaf buds.*—Pointed, medium.

Flower buds:

- *Hardiness.*—Hardy, with respect to central California winters.
- *Diameter.*—Typically, 3/16" [4.8 mm.] 1 week before bloom.
- *Length.*—Typically, ⅜" [9.5 mm.] 1 week before bloom.
- *Form.*—Not appressed.
- *Surface.*—Pubescent.
- *Tip color.*—White [263. White].

Flowers: Perfect, complete, perigynous, usually a single pistil, typically thirty or more stamens, five sepals and petal locations alternately positioned.

- *Average flower diameter.*—1" [25.4].
- *Number of petals.*—Five, no double blossoms observed.
- *Petal shape.*—Oval to circular.
- *Petal margin.*—Entire, smooth, slightly wavy.
- *Average petal diameter.*—½" [12.7 mm.].
- *Average petal length.*—9/16" [14.3 mm.].
- *Petal apex.*—Rounded.
- *Petal base.*—Obtuse.
- *Petal color.*—White [263. White] on both sides.
- *Anther color.*—Strong orange [50. s.O] over Very yellow [83. v.Y].
- *Stigma color.*—Light greenish yellow [101. l.gY].
- *Sepal color.*—Light yellow green [119. l.YG].
- *Sepal length.*—5/32" [4.0 mm.].
- *Sepal width.*—5/32" [4.0 mm.].
- *Sepal apex.*—Rounded to elliptical to match the width and length.

*Sepal margin.*—Fairly smooth to the naked eye, slightly serrate when magnified.
*Average pistil length.*—⅝" [15.9 mm.].
*Average stamen length.*—½" [12.7 mm.].
*Fragrance.*—Moderate.
*Pollen production.*—Very heavy, bee enticing.
*Blooming period.*—Early, three days before 'AMBRA' plum (unpatented).
*Onset of bloom.*—One percent on Feb. 19, 2007.
*Date of full bloom.*—Mar. 2, 2007.
*Duration of bloom.*—One to two weeks, dependent on ambient temperature.
*Bloom density.*—Heavy.
*Number per cluster.*—2 to 10, average 4.

Fruit

Maturity when described: Firm ripe, Jun. 12, 2007.
Date of first picking: Jun. 1, 2007.
Date of last picking: Jun. 12, 2007.
Size: Uniform, Medium.
*Average diameter axially.*—2" [50.8 mm.].
*Average diameter across cheek plane.*—2⅜" [60.3 mm.].
*Average diameter across suture plane.*—2⅜" [60.3 mm.].
*Typical weight.*—4.1 ounces [116 grams].
Form: Uniform, oblate, symmetrical.
*Longitudinal section form.*—Round.
*Transverse section through diameter.*—Very oblate.
Suture: An inconspicuous line located in a very shallow groove extending from the base to just past the apex.
Ventral surface: Rounded, slightly lipped toward the base.
Lips: Equal.
Cavity: Flaring, circular, suture showing on one side, Moderate purplish red [258. m.pR] stem markings typical.
*Depth.*—5/16" [7.9 mm.].
*Breadth.*—¾" [19.1 mm.].
Base: Truncate, somewhat cordate if viewed parallel to the suture.
Apex: Very truncate with a moderate depression at the pistil point.
Pistil point: An inconspicuous dot.
Stem: Medium.
*Average length.*—⅜" [9.5 mm.].
*Average width.*—5/64" [2.0 mm.].
Skin:
*Thickness.*—Medium.
*Surface.*—Smooth.
*Tenacity.*—Tenacious to the flesh.
*Astringency.*—Slight.
*Tendency to crack.*—Slight.
*Color.*—Blackish red [21. blackish R] with just a minor amount of very small Pale pink [7. p.PK] freckling throughout.
*Bloom.*—Abundant.
Flesh:
*Color.*—Very red [11. v.R] toward the stone, Dark red [16. d.R] toward the skin.
*Surface of pit cavity.*—Covered with Deep red [13. deep R] broken fibers when twisted from the stone.
*Amygdalin.*—Moderate.
*Juice.*—Moderate, rich.
*Texture.*—Firm, crisp.
*Fibers.*—Abundant, fine, tender.
*Ripens.*—Slightly earlier toward the apex.
*Flavor.*—Acidic with moderate sugar, typically 15–18 brix.
*Aroma.*—Moderate.
*Eating quality.*—Good.

Stone

Type: Clingstone.
Form: Oval.
Hilum: Narrow.
Base: Rounded.
Apex: Rounded, most having a sharp 1/16" [1.6 mm] tip.
Sides: Equal.
Surface: Rough throughput with one groove from base to apex on each side of the dorsal fin.
External color of stone: Moderate orange yellow [71. m.OY].
Pit wall color when cracked: Light yellowish brown [76. l.yBr].
Cavity surface color: Light yellowish brown [76. l.yBr].
Average pit wall thickness: 1/16" [1.6 mm.]
Average width: 9/16" [14.3 mm.].
Average length: ⅝" [15.9 mm.].
Average breadth: 5/16" [7.9 mm.].
Tendency to split: None observed.
Kernel:
*Form.*—Oval.
*Skin color.*—Moderate orange yellow [71. m.OY] when first removed.
*Pellicle color.*—Dark orange yellow [72. d.OY].
*Vein color.*—Dark orange yellow [72. d.OY].
*Taste.*—Bitter.
*Viable.*—Yes.
*Average width.*—¼" [6.4 mm.].
*Average length.*—⅜" [9.5 mm.].
*Amygdalin.*—Moderate.

Use

Market: Fresh market and long distance shipping.
Keeping quality: Good, fruit quality observed to remain in good condition after 21 days in standard cold room at 36° Fahrenheit [2° Celcius].
Shipping quality: Good.
Resistance to insects: No unusual susceptibilities noted.
Resistance to diseases: No unusual susceptibilities noted.

Other notes

Although the new variety of interspecific tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of interspecific *Prunus* sp. tree, substantially as illustrated and described, that is similar to 'YUMMY® gem' (U.S. Plant Pat. No. 15,809) plum by being self-unfruitful, by blooming during the early season, and by producing fruit that is almost black in skin color, but is distinguished therefrom by producing fruit that is larger in size, oblate instead of globose in shape, and fully red in flesh color instead of yellow.

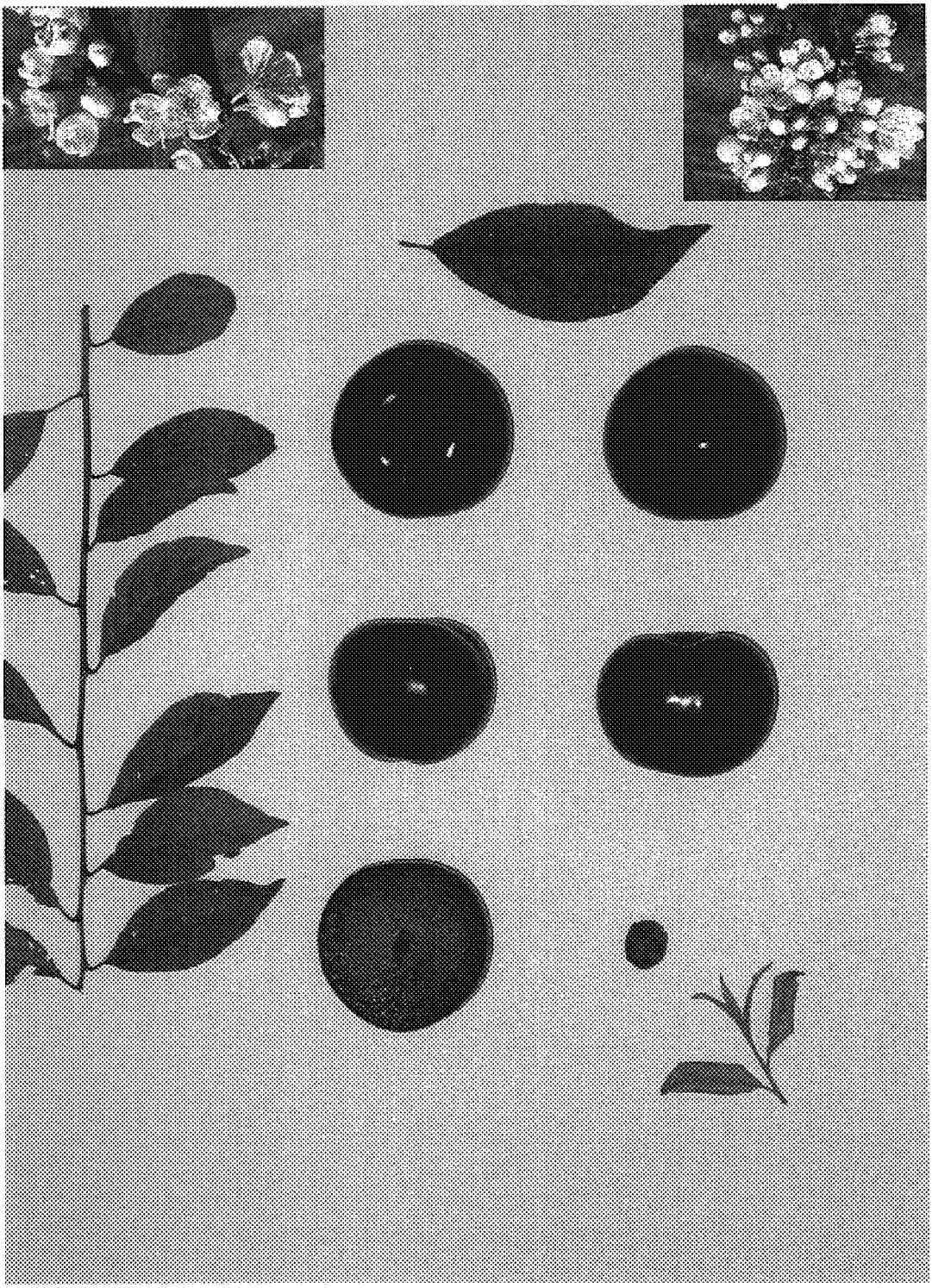

* * * * *